United States Patent [19]

Razran

[11] 4,181,407

[45] Jan. 1, 1980

[54] APPARATUS FOR AUTOMATICALLY TESTING VISION BY PHASE MEASUREMENTS

[76] Inventor: Gilbert B. Razran, P.O. Box 207, Del Mar, Calif. 92014

[21] Appl. No.: 921,838

[22] Filed: Jul. 3, 1978

[51] Int. Cl.² .............................................. A61B 3/10
[52] U.S. Cl. .......................................... 351/6; 351/13; 351/16
[58] Field of Search ............................ 351/6, 13, 16; 128/2.1 B

[56] References Cited

U.S. PATENT DOCUMENTS 3,574,450  4/1971  White ..................................... 351/17

*Primary Examiner*—John K. Corbin
*Assistant Examiner*—Rodney B. Bovernick
*Attorney, Agent, or Firm*—Brown & Martin

[57] ABSTRACT

Apparatus for automatically testing a patient's vision includes a target, at least one lens, and an eyepiece serially aligned along one optical path. A motorized drive circuit moves the target or lens to selectable positions along the optical path in response to first digital control signals; while a light drive circuit enables light stimulus to be directed along the optical path through the target, lens and eyepiece at each selectable position in response to second digital control signals.

A digital control circuit has outputs coupled to the motorized drive circuit and to the light drive circuit for generating the first and second digital control signals in a predetermined sequence. Inputs on the control circuit receive electrical signals evoked in the brain of the patient by to the light stimulus. The control circuit measures the time delay between said light stimulus and said evoked response at each of said selectable positions, and generates a corrective prescription based on the selectable position which yields the longest response time.

9 Claims, 9 Drawing Figures

APPARATUS FOR AUTOMATICALLY TESTING VISION BY PHASE MEASUREMENTS

BACKGROUND OF THE INVENTION

This invention relates to vision testing equipment and, more particularly to apparatus for automatically generating eye glass prescriptions to correct faulty vision. In the past, one way to test vision was to have the patient read an eye chart, through a series of graded lenses. Using this technique, an eye glass prescription is determined from the patient's comments as to which lens produces the most clear image. This procedure however, has the undesirable characteristic of being dependent upon the patient's subjective opinion. Further vision correcting by this procedure takes a relatively long time. This is because the lens changing is manually performed, and because a large number of subjective opinions is usually required to be elicited from the patient before the optimal lens prescription can be determined.

In an attempt to overcome the above described and other deficiencies, various other vision testers have been devised. One such tester is disclosed in the U.S. Pat. No. 3,574,450 which was issued to Carol T. White in 1971. That vision tester presents a light stimulus through a graded series of lenses, and it further includes a computer having inputs which are coupled to receive voltage response signals from the patient's brain. In operation, the light stimulus is passed through one of the lenses and the magnitude of the evoked response is measured and remembered by the computer. Subsequently, a differently graded lens is manually selected and the steps are repeated. After a response has been measured through all of the lens, the computer calculates which of the evoked responses have the largest amplitude. Then the lens corresponding to that evoked response is indicated as giving the best visual correction.

Another prior art automatic vision testing device called "Dioptron" has been developed by Coherent Radiation Corporation of Palo Alto, Calif. This device passes a beam of light through a lens into the patient's eye, and includes apparatus for detecting the angle at which the light is reflected from the patient's retina. The angular information is fed to a computer; and based thereon, the computer calculates the lens prescription for the patient.

All of these devices have deficiencies however, which are overcome by the disclosed invention. For example, the apparatus in U.S. Pat. No. 3,574,450 includes a graded series of lenses which are manually selected during the testing process. Accordingly, testing vision with the apparatus disclosed therein is not fully automatic and is relatively slow. Similarly, the Dioptron tester is deficient in that is does not utilize signals evoked in the brain to determine the lens correction. Instead it utilizes signals which are derived from the mechanical characteristics of the eyeball. As such, the results obtained do not take into consideration the effect of the optic nerve, the optic chiasm, the occipital lobe, and other parts of the brain which affect the patient's total vision. Further, the disclosed invention differs from both U.S. Pat. No. 3,574,450 and the Dioptron device in that it utilizes a totally different signal processing scheme to determine a lens prescription. In particular, the disclosed invention processes variations in time lapse that occurs between an input stimulus to the eye and an evoked response in the brain. That is, the disclosed invention processes phase as opposed to magnitude of the evoked response.

Therefore, it is one object of the invention to provide improved apparatus for automatically testing spatial vision.

Still another object of the invention to provide a controller for automatically testing vision based on a variable time delay which occurs between applications of a light stimulus to the eye and an evoked response from the brain.

SUMMARY OF THE INVENTION

These and other objectives are accomplished in accordance with the invention by a controller which includes an optical mechanism containing a target, at least one lens, and an eyepiece. This target, lens, and eyepiece are aligned along one optical path. Either the target or lens have selectable positions on this path.

Also included are motorized drive circuits and a light emitting circuit. The motorized driver circuits move the target or lens to the selectable positions along the optical paths in response to predetermined digital control signals. Similarly, the light circuit enables a light stimulus to be directed through the target, lens and eyepiece in response to other predetermined digital control signals.

The controller further includes a digital control circuit. It has outputs coupled to the motorized driver circuit and the light circuit; and it generates the predetermined digital control signals on these outputs. These signals are generated in a sequence such that the lens or target is moved to various positions along the optical path and a light stimulus is enabled at each of these positions.

The digital control circuit also has inputs for receiving electrical signals evoked in the patient's brain by the light stimulus. These evoked signals are used by the digital control circuit to determine a corrective lens prescription. In particular, the digital control circuit measures the time delay between the light stimulus and the evoked response at each of the various positions for the lens and target; and the corrective prescription is based on which of these time delays is the longest.

BRIEF DESCRIPTION OF THE DRAWINGS

The novel features believed characteristic of the invention are set forth in the appended claims; the invention itself, however, as well as other features and advantages thereof, will best be understood by reference to the following detailed description of preferred embodiments, when read in conjunction with the accompanying drawings, wherein:

DETAILED DESCRIPTION

Figure 1:
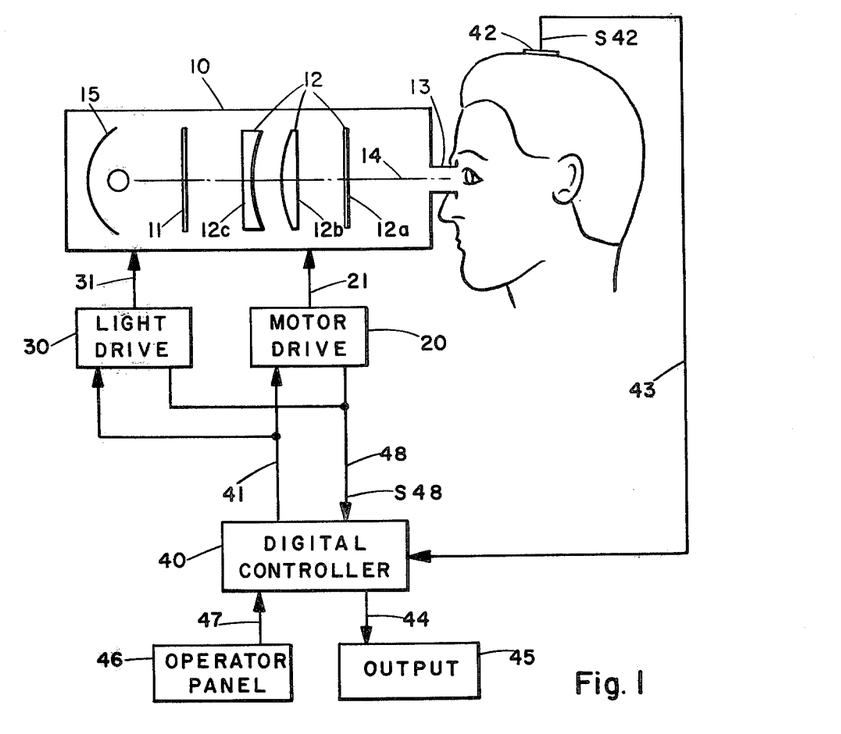
FIG. 1 is a block diagram of apparatus constructed according to the invention for automatically testing vision and calculating corrective lens prescriptions.

Referring now to FIG. 1, there is illustrated a block diagram of vision testing apparatus constructed according to the invention. Included therein as one portion of this apparatus is as optical lens system 10. This lens system is comprised of a target 11, at least one lens 12, and an eye piece 13 respectively aligned along one optical path 14. In general, target 11 and/or lens 12 are movable along path 14 in a manner that is suitable for testing either spherical correction, cylindrical correction, axial correction, or any combination thereof. Preferably, lens 12 include a spherical lens 12a, a plano convex lens 12b, and a plano concave lens 12c as illustrated.

Basically, spherical correction is determined by moving target 11 along path 14; cylindrical correction is determined by moving lens 12c along path 14; and axial correction is determined by rotating lens 12b and 12c about path 14. Also included within lens system 10 is a strobe light 15 which provides a light stimulus to be directed through target 11 and lens 12 into eye piece 13. In operation, target 11 and lens 12 are iteratively positioned along path 14; and light 15 provides a light stimulus at each of these positions.

A motorized drive circuit 20 couples via leads 21 to lens system 10; and similarly, a light drive circuit 30 couples via leads 31 to the lens system. Drive circuit 20 sequentially moves target 11 and lens 12 to various selectable positions along path 14 in response to digital control signals on leads 41. These signals are generated by a digital control circuit 40. Similarly circuit 30 causes light to be emitted from strobe light 15 and directed through target 11 and 12 at each of the various positions in response to other digital control signals on leads 41 for control circuit 40.

In operation, control circuit 40 moves target 11 and lens 12 to one predetermined position by sending appropriate control signals to drive circuit 20. Subsequently, control circuit 40 causes multiple strobes of light to be passed through the positioned target and lens. In response to these strobes of light, electrical signals are evoked in the patients brain. These signals are detected by the electrodes 42 on the patients scalp; and are fed to control circuit 40 via leads 43.

There, the phase relation between the control signals that cause the light stimulus, and the evoked response is measured and stored. This measurement is made several times (10 or 20 times) for each particular position of target 11 and lens 12. These measurements are then averaged by control circuit 40 and stored for further computation.

Subsequently, control circuit 40 sends control signals to drive circuit 20 which move target 11 and lens 12 to a new position. Then control circuit 40 causes light stimulus to be emitted by circuit 30, and repeats the averaging sequence as described above. After the averaged evoked response for each of a plurality of lens and target positions has been stored, control circuit 40 analyzes the data in a manner to be described in conjunction with FIG. 5. Based on this analysis circuit 40 manifests the patients lens prescription by signals on leads 44 to an output device 45. In one preferred embodiment, output device 45 is a digital display. There, digits are selectively illuminated to display numbers indicating the spherical correction and cylindrical correction in diopters, and the axial correction in degrees.

An operator panel 46 also couples to controller 40 via leads 47. Panel 46 provides a means for manually initiating the above described functions. Suitably, panel 46 includes a plurality of switches that enable an operator to start the test, stop the test, and power the apparatus on and off.

Figure 2:
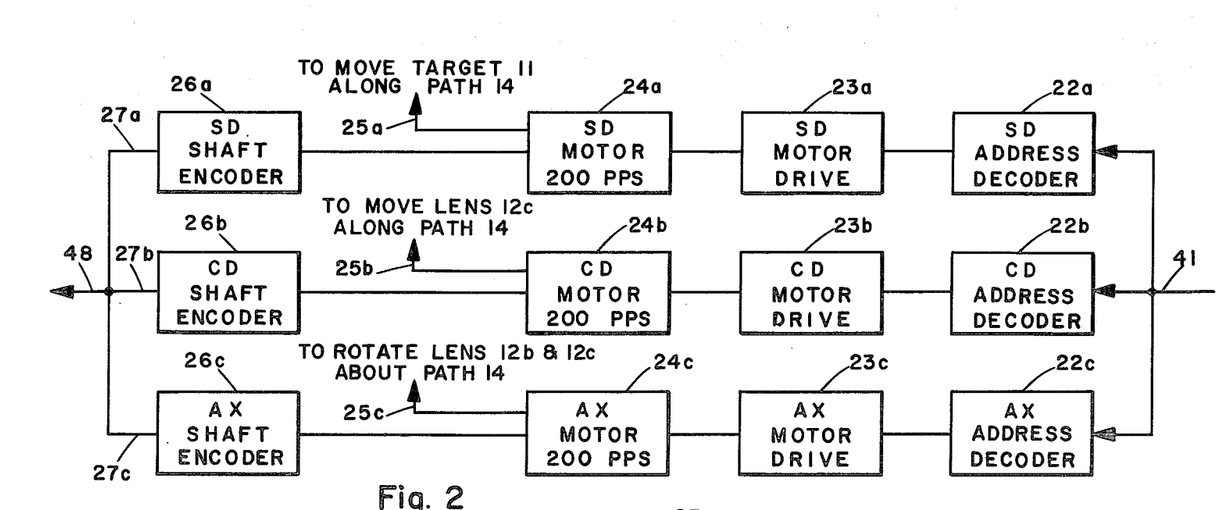
FIG. 2 is a block diagram illustrating the components of a motorized drive circuit within the apparatus of FIG. 1.

Further details of drive circuit 20 and light drive circuit 30 will now be described in conjunction with FIG. 2. As therein illustrated, circuit 20 includes a plurality of address decoders 22a–22c. Leads 41 coupled to inputs on these decoders, which operate to detect predetermined combinations of digital signals on their inputs and generate output signals in response thereto.

Drive circuit 30 also includes pulse generators 23a–23c having inputs that are respectively coupled to the outputs of address decoders 22a–22c. The pulses produced by these generators are received by stepping motors 24a–24c. Motor 24a has a shaft 25a which couples to and moves target 11. Similarly, motor 24b has a shaft 25b which couples to and moves cylindrical lens 12c; while motor 24c has a shaft 25c which couples to and moves lens 12c and 12b.

In operation, target 11 is moved along path 14 in response to predetermined logic signals which are detected by address decoder 22a. This decoder activates generator 23a which send pulses of a predetermined width to motor 24a. In response to these pulses, motor 24a moves target 11 by a predetermined distance. Lens 12c is moved along path 14; and lens 12b and 12c are rotated about path 14 by similar sequences initiated by decoders 22b and 22c.

Drive circuit 30 also includes shaft encoders 26a–26c which respectively couple to motors 24a–24c. These encoders have output 27a–27c which are coupled back to digital controller 40 via leads 48. In operation, the encoders generate logic signals on their respective outputs indicating the position of the shaft of the motor to which they are coupled. Thus, encoders 26a–26c provide a means by which controller 40 may sense the result of an operation which it initiated by control signals on leads 41.

Figure 3:
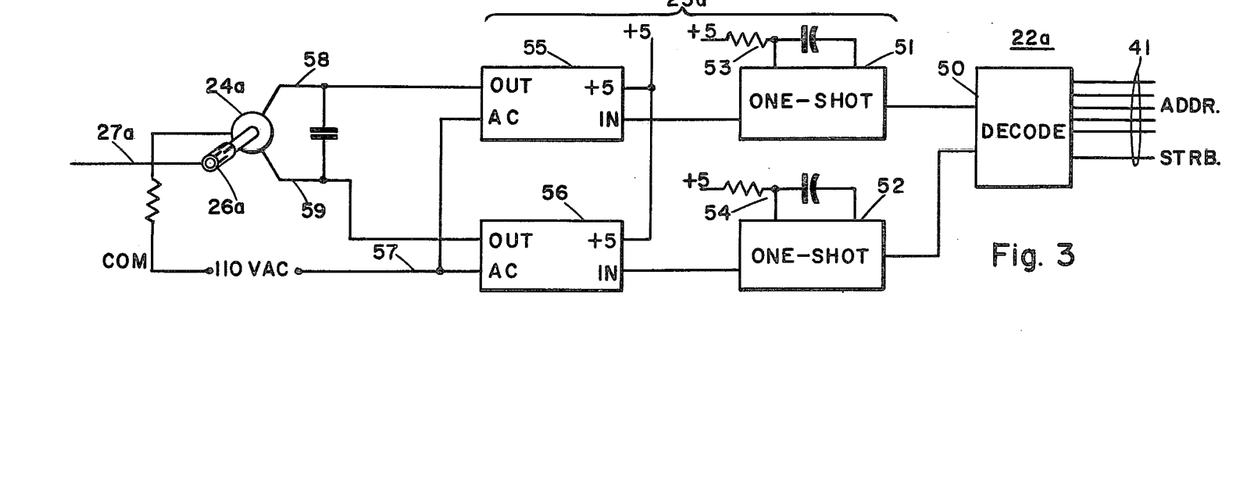
FIG. 3 is a detailed logic diagram of a portion of the motorized drive circuit of FIG. 2.

Next, referring to FIG. 3, a detailed logic diagram of components 22a–27a of FIG. 2 will be described. Components 22b–27b, and components 22c–27c are similar in structure, and thus a detailed drawing of them is not separately included. As illustrated in FIG. 3, decoder 22a consists of a single semiconductor chip 50. Chip 50 is a one-out-of-eight decoder, such as a $T^2L$ 74136 as an example. Leads 41 coupled to inputs of chip 50; and the chip operates to decode various binary combinations of the input signals.

One of the decode outputs from chip 50 couples to the triggering input of a one-shot circuit 51; while another output couples to the triggering input of a second one-shot circuit 52. Suitably, these circuits consist of a $T^2L$ 74123. Circuits 51 and 52 respectively have an RC timing circuit 53 and 54 coupled thereto. The actual values of the resistor and capacitor in these timing circuits determine the width of the output pulse from the one-shots.

The outputs of one-shots 51 and 52 connect to the control inputs of solid state relay circuits 55 and 56. In operation, relay 55 couples a 110 volt AC source at 57 to one terminal 58 of motor 24a; while relay 56 couples the 110 volt AC source to a second terminal 59 of the motor. Application of the 110 volts to terminal 58 causes motor 24a to move target 11 further away from lens 12c; while application of the 110 volts to terminal 59 causes motor 24a to move target 11 closer to lens 12c. The exact amount of movement of the lens is directly proportional to the length of time which the 110 volts is applied to the terminals; and this in turn is directly proportional to the width of the pulse from one-shots 51 and 52. A variety of stepping motors will suitably respond to the pulses from relays 55 and 56. In one embodiment, a 1/500 horsepower, shaded pole motor was used.

Figure 4:
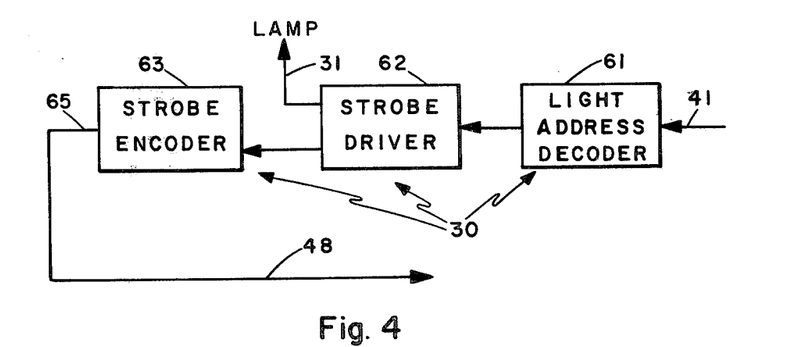
FIG. 4 is a detailed block diagram of the light enabling circuit within the apparatus of FIG. 1.

Next, with reference to FIG. 4, the details of light drive circuit 30 will be described. Basically, circuit 30 is comprised of an address decoder 61, a strobe drive circuit 62, and a feedback circuit 63. Address decoder 61 has inputs coupled to receive logical control signals from leads 41; and it operates to detect predetermined logical signals on those leads. Output signals from decoder 61 activate driver circuit 62, which in turn activate strobe light 15. Feedback circuit 63 generates digital signals on an output 65 which couples to leads 48 for detection by controller 40. This structure allows controller 40 to receive timing signals indicating a precise reference point at which the patient is subjected to the light stimulus.

The light stimulus emitted by strobe light 15 passes into the patient's retina and causes responses in the patient's brain which are detected by electrodes 42. More specifically, signals from the retina of each eye are transmitted down the optic nerve to the optic chiasma. There electrical signals from the right field of vision pass to the left half of the brain; and electrical signals from the left field of vision pass to the right half of the brain. From there the electrical signals pass through the thalamus and lateral geniculate to the striate area of the occipital lobe. As signals pass along the above described paths, various processing and functions are performed thereon by the brain. In the present invention, this activity is monitored by electrode 42. Preferably, this electrode is placed on the exterior of the scalp about one centimeter to the right or to the left above the inion. A second electrode preferably is also used as a reference; and it is placed on the ear over the temporal lobe.

Figure 5:
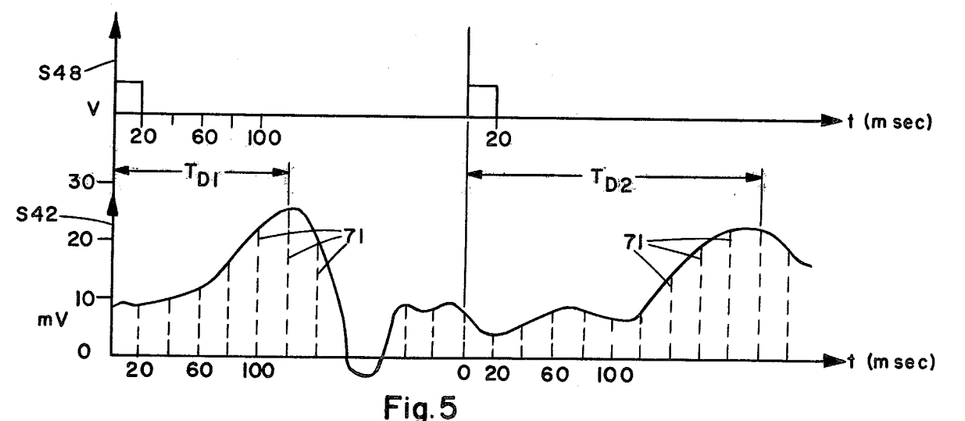
FIG. 5 is a set of curves illustrating signals at various points within the apparatus of FIG. 1.

FIG. 5 is a set of curves illustrating various evoked response signals which are detected by electrode 42, as well as feedback timing signals on leads 48. The former are illustrated as S42, and the latter as S48. Typically, signal S48 is a rectangular shaped pulse having a width of approximately 20 milliseconds. These pulses are repeated at some convenient repetition rate, such as one pulse every 240 milliseconds.

The present invention operates on the principal that clearness of vision is indicated by the time delays between the reference signal S48 and the occurrence of the evoked response S42. Clearest vision is indicated by a relatively long time delay; whereas blurred vision is indicated by a relative short time delay. This effect is explained by the theory that the brain requires more time to process signals along the optic track when those signals represent clearly perceived images, than when those signals represent blurred images.

To determine the time delay of an evoked response, controller 40 samples signal S42 and obtains samples 71. A sampling rate of 20 milliseconds per sample is suitable. In addition, controller 40 takes multiple readings for each particular setting of target 11 and lens 12. Ten or twenty such readings have been found suitable.

As indicated in FIG. 5, each particular evoked response falls easily within approximately 240 milliseconds. Thus twenty such evoked responses fall within 4.6 seconds, which is quite fast for the eye test. Samples from the twenty evoked responses are then averaged by controller 20; and then the average time delay is calculated. This average time delay is stored for future reference and comparison with other similarly calculated time delays obtained at different target and lens settings.

Figure 6:
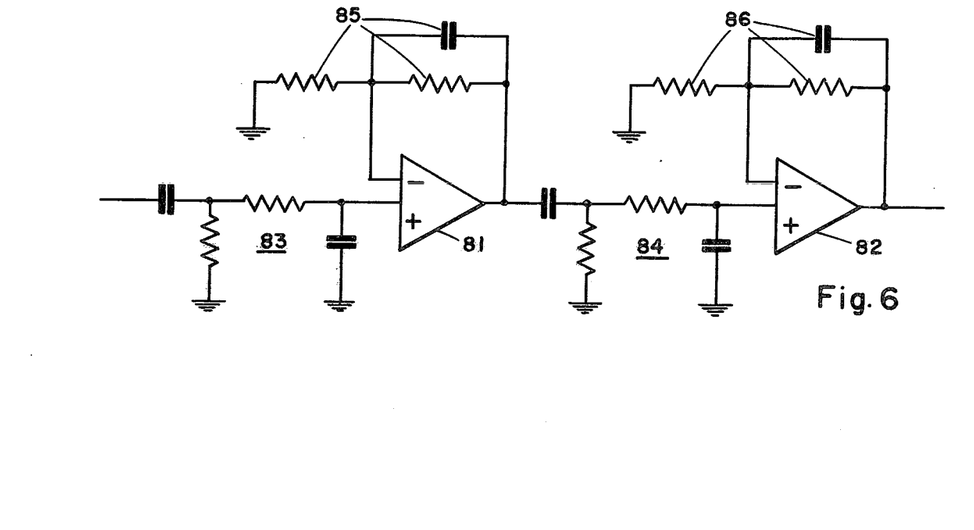
FIG. 6 is a detailed circuit diagram of an evoked response input amplifier within the apparatus of FIG. 1.

Preferably, before the signals detected by electrodes 42 are sampled, they are amplified. This is because they generally are no larger than 30 microvolts. FIG. 6 is a diagram of a circuit suitable for amplifying signals S42. This circuit has a gain of approximately $1.0 \times 10^5$. Basically, the circuit is comprised of operational amplifiers 81 and 82. Low pass filters 83 and 84 respectively connect to the inputs on amplifiers 81 and 82, and they have a cutoff frequency at approximately 30 HZ. Feedback circuits 85 and 86 respectively connect to operational amplifiers 81 and 82 to determine the gain of each of these amplifiers. Resistance and capacitances of the values indicated in FIG. 6 may be utilized to achieve the above described gain and frequency characteristics.

Figure 7:
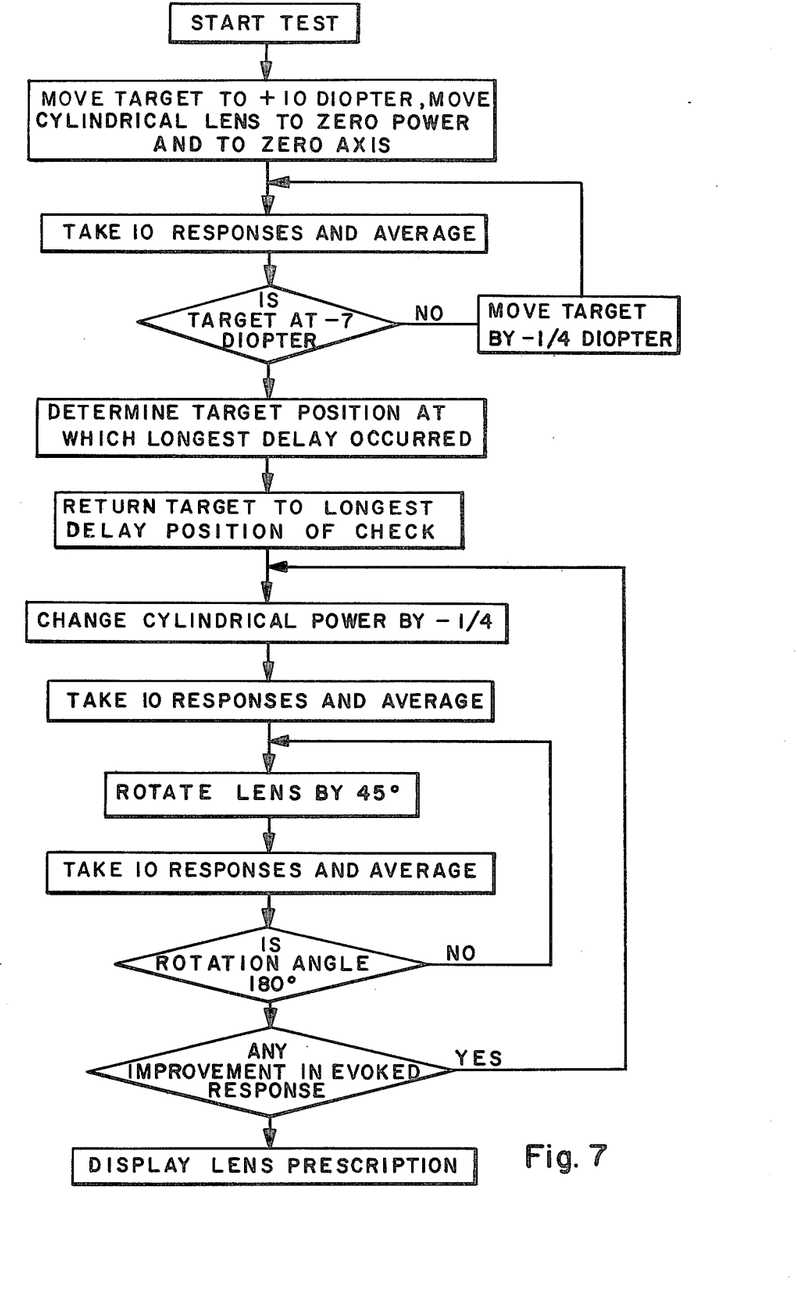
FIG. 7 is a flow diagram illustrating various sequences directed by a digital control circuit within the apparatus of FIG. 1.

In FIG. 7, there is illustrated a flow diagram describing a series of steps which digital controller 40 performs during a vision test. At the start of the test, controller 40 moves target 11 to a +15 diopter position along path 14; moves cylindrical lens 12c and 12b to a zero power position; and rotates cylindrical lens 12c and 12b to a zero degree setting about path 14. These steps are performed by motorized drive circuits 20 and 30 in response to control signals on leads 41 as was previously described.

Subsequently, logical controller 40 activates light drive circuit 30 and measures the response evoked from the patient on electrodes 42. Ten responses are evoked; and the average of these responses is calculated by logical controller 40. Then target 11 is moved by a ¼ diopter; and ten new responses are taken and averaged at the new target setting. These steps are repeated until target 11 has moved to a −10 diopter position along paths 14.

Next, control circuit 40 operates on each of the averaged responses to determine the target position at which the longest delay in the evoked response occurred. After making this calculation, the target is returned to that position and the long response time is verified. Upon verification, control circuit 40 has all of the information necessary to calculate a prescription for spherical lens correction.

The remaining steps performed by controller 40 are made to determine the required cylindrical correction and axial correction. To this end, controller 40 takes averaged readings with the cylindrical power of lens 12b and 12c being changed in steps of ¼ diopter, and the axial orientation of lens 12b and 12c being rotated to 0°, 45°, 90°, and 135°. At each cylindrical power setting, the averaged evoked responses are compared with corresponding previous responses to determine which gave the longest delay. If any increase occurs, the cylindrical power is again changed by a −¼ diopter and the testing continues. Conversely, if no increase occurs, testing ceases; and controller 40 displays the lens prescription corresponding to the longest delay via output circuit 45.

Each of the above described steps may be carried out by special purpose hardwired logic circuitry; or alternatively, may be carried out by a general purpose computer. Using the latter, it is only necessary that the processor have the capability to transmit and receive messages from external circuits such as 20, 30, and 42; and have computing capability sufficient to perform the above described decision making and averaging. In one preferred embodiment, control circuit 40 is a PDP 11/40 computer. A listing of a program in RT-11 compiler language for this computer which performs the above tasks is given in Table 1.

Figures 8A, 8B:
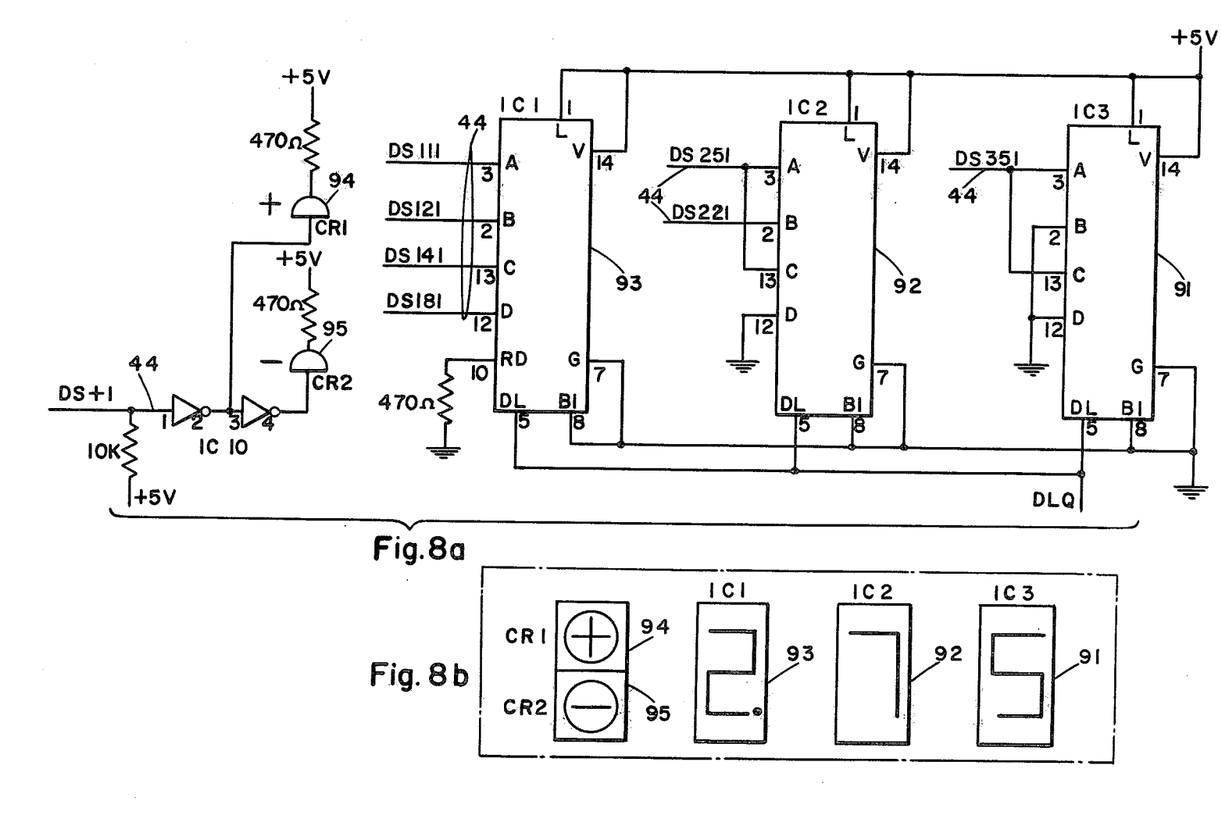
FIG. 8 is a logic diagram of a portion of the output circuit within the apparatus of FIG. 1.

Details of one preferred output circuit 45 is illustrated in FIG. 8. Specifically, FIG. 8a is a detailed logic diagram illustrating circuit interconnections while FIG. 8b is a pictorial diagram illustrating the output circuit as viewed by the operator. In this circuit, numeric display chips 91–93 and individual light emitting diodes 94–95 display the calculated lens prescription. Specifically, chips 91–93 display the numerical amount of spherical correction required; while diodes 94 and 95 display whether near-sighted or far-sighted correction is required. Output circuit 45 preferably also includes second and third circuits similar to those illustrated in FIG. 8A. These respectively display cylindrical correction and axial correction. TI-TI/311 chips may suitably be used as chips 91–93.

Various embodiments of the invention have now been described in detail. Further, many changes and modifications can be made to the above described details without departing from the nature and spirit of the invention. For example, the strobe light 15 may be replaced by a light of constant luminance with the visual stimulus being provided by a target 11 which periodically changes its position. For example, target 11 may include a checkboard pattern of black and white squares which alternately change position. Utilizing this pattern shifting, any effect on the evoked response of the intensity of the strobe light is minimized.

TABLE I

| Reference Number | | Instructions | | Comments |
|---|---|---|---|---|
| | Main Memory Address | | Operands | |
| 452 | 0001 | DIAG: LDA | .SW1 | ;GET SWITCH BUFFER 1 |
| 453 | 0004 | CMA | | |
| 454 | 0005 | DISPA | .1CNTDSP; | DISPLAY IN LEFT COUNT |
| 455 | 0017 | LDA | .SW2 | ;GET SWITCH BUFFER 2 |
| 456 | 0022 | CMA | | |
| 457 | 0023 | DISPA | .3CNTDSP; | DISPLAY IN RIGHT COUNT |
| 458 | 0035 | LDA | .SW3 | ;GET SWITCH BUFFER 3 |
| 459 | 0040 | CMA | | |
| 460 | 0041 | DISPA | .1LATDSP; | DISPLAY IN LEFT LATENCY |
| 461 | 0053 | LDA | .SW4 | ;GET SWITCH BUFFER 4 |
| 462 | 0056 | CMA | | |
| 463 | 0057 | DISPA | .3LATDSP; | DISPLAY IN RIGHT LATENCY |
| 464 | 0071 | LDA | .CHAN1 | ;GET CHANNEL 1 INPUT |
| 465 | 0074 | STA | .XOUT | ;OUTPUT IT TO X |
| 466 | 0077 | DISPA | .1AMPDSP; | DISPLAY IT IN LEFT AMPLITUDE |
| 467 | 0111 | LDA | .CHAN2 | ;GET CHANNEL 2 INPUT |
| 468 | 0114 | STA | .YOUT | ;OUTPUT IT TO Y |
| 469 | 0117 | DISPA | .3AMPDSP; | DISPLAY IT IN RIGHT AMPLITUDE |
| 470 | | ; | | |
| 471 | 0131 | LDA | .SW1 | |
| 472 | 0134 | CMA | | |
| 473 | 0135 | MOV | B,A | ;SAVE A |
| 474 | 0136 | ANI | $PLOT | ;SEE IF PLOT SWITCH PRESSED |
| 475 | 0140 | SUI | 1 | |
| 476 | 0142 | JM | 1$ | ;IF NOT, DISABLE PLOT OUTPUTS |
| 477 | 0145 | JP | 2$ | ;IF IT IS, ENABLE PLOT OUTPUTS |
| 478 | 0150 | 3$: MOV | A,B | ;RESTORE A |
| 479 | 0151 | ANI | $START | ;SEE IF START SWITCH PRESSED |
| 480 | 0153 | SUI | 1 | |
| 481 | 0155 | JM | DIAG | ;IF NOT, CONTINUE DIAGNOSTIC |
| 482 | 0160 | JP | MEMTST | ;IF IT IS, GO DO MEMORY TEST |
| 483 | | ; | | |
| 484 | 0163 | 1$: STA | .OFFPLOT; | DISABLE PLOT OUTPUTS |
| 485 | 0166 | JMP | 3$ | |
| 486 | 0171 | 2$: STA | .ONPLOT | ;ENABLE PLOT OUTPUTS |
| 487 | 0174 | JMP | 3$ | |
| 505 | 0177 | MEMTST: XRA | A | ;CLEAR A |

```
506 0200                MOV     C,A       ;INITIALIZE PASSES COMPLETED
507 0201        1$:     LXI     H,MEMST   ;POINT TO START OF MEMORY
508 0204                MOV     A,C       ;INITIALIZE PATTERN
509 0205        2$:     MOV     M,A       ;STORE PATTERN TO MEMORY
510 0206                MOV     E,A       ;SAVE A
511 0207                DISPA   .3CNTDSP  ;DISPLAY PATTERN BEING STORED
512 0221                MOV     A,H       ;DISPLAY ADDRESS STORED TO
513 0222                DISPA   .1LATDSP
514 0234                MOV     A,L
515 0235                DISPA   .3LATDSP
516 0247                MOV     A,E       ;RESTORE A
517 0250                ADI     1         ;INCREMENT PATTERN
518 0252                DAA               ;MAKE IT DECIMAL
519 0253                INX     H         ;INCREMENT ADDRESS
520 0254                MOV     E,A       ;SAVE A
521 0255                MOV     A,H       ;GET HI BYTE OF ADDRESS
522 0256                CPI     MEMEND    ;SEE IF MEMORY FILLED WITH PATTERNS
523 0260                MOV     A,E       ;RESTORE A
524 0261                JNZ     2$        ;CONTINUE IF NOT YET FILLED
525             ;
526 0264        3$:     LXI     H,MEMST   ;POINT BACK TO START OF MEMORY
527 0267                MOV     A,C       ;RE-INITIALIZE PATTERN
528 0270        4$:     MOV     D,M       ;READ WHAT WAS STORED IN MEMORY
529 0271                MOV     E,A       ;SAVE A
530 0272                DISPA   .1AMFDSP  ;DISPLAY WHAT SHOULD HAVE BEEN READ
531 0304                MOV     A,D       ;DISPLAY WHAT WAS READ
532 0305                DISPA   .3AMFDSP
533 0317                MOV     A,H       ;DISPLAY ADDRESS READ FROM
534 0320                DISPA   .1LATDSP
535 0332                MOV     A,L
536 0333                DISPA   .3LATDSP
537 0345                MOV     A,E       ;RESTORE A
538 0346                CMP     D         ;COMPARE EXPECTED TO ACTUAL
539 0347                JZ      6$        ;IF EQUAL, CONTINUE
540 0352        5$:     LDA     .SW1      ;ELSE, ERROR, LOOK AT START SWITCH
541 0355                CMA               ;MAKE CLOSED=1
542 0356                ANI     $START    ;GET START BIT
543 0360                SUI     1
544 0362                JM      5$        ;HANG UNTIL START SWITCH PRESSED
545 0365                MOV     A,E       ;RESTORE A
546 0366        6$:     ADI     1         ;INCREMENT PATTERN
547 0370                DAA               ;MAKE IT DECIMAL
548 0371                INX     H         ;INCREMENT ADDRESS TO TEST
549 0372                MOV     E,A       ;SAVE A
550 0373                MOV     A,H       ;GET HI BYTE OF ADDRESS
551 0374                CPI     MEMEND    ;SEE IF ALL OF MEMORY SCANNED
552 0376                MOV     A,E       ;RESTORE A
553 0377                JNZ     4$        ;CONTINUE IF NOT ALL SCANNED
554             ;
555 0402                MOV     A,C       ;GET COUNT OF PASSES
556 0403                ADI     1         ;INCREMENT IT
557 0405                DAA               ;MAKE IT DECIMAL
558 0406                MOV     C,A       ;PUT IT BACK
559 0407                DISPA   .1CNTDSP  ;DISPLAY IT
560 0421                JMP     1$        ;AND CONTINUE TESTING
568 0424        BINDEC: MVI     C,16      ;SET COUNT OF BITS LEFT
569 0426                LXI     D,0       ;CLEAR DECIMAL
570 0431                MOV     A,H       ;IF BINARY
571 0432                ORA     L         ; IS ZERO,
572 0433                RZ                ;   THEN DONE
573 0434        1$:     DAD     H         ;ELSE SHIFT BIT OUT
574 0435                DCR     C         ;DECREMENT BIT COUNT
575 0436                JNC     1$        ;AND CONTINUE UNTIL A 1 BIT APPEARS
576             ;
577 0441        2$:     MOV     A,E       ;DOUBLE DECIMAL, ADD 0 OR 1 BIT
578 0442                ADC     A
579 0443                DAA
580 0444                MOV     E,A
581 0445                MOV     A,D
```

```
582 0446                    ADC     A
583 0447                    DAA
584 0450                    MOV     D,A
585 0451                    RC              ;RETURN WITH CARRY SET IF OVERFLOW
586 0452                    DAD     H       ;ELSE GET NEXT BIT INTO CARRY
587 0453                    DCR     C       ;DECREMENT BIT COUNT
588 0454                    JP      2$      ;CONTINUE IF NOT PAST LAST BIT
589 0457                    RET             ;ELSE RETURN WITH CARRY OFF
590                         ;
```

MAIN    RT-11 MACRO
SYMBOL TABLE.

| | | |
|---|---|---|
| A     = 000007 | B     = 000000 | BINDEC 000424 |
| C     = 000001 | D     = 000002 | DIAG   000001 |
| E     = 000003 | H     = 000004 | L     = 000005 |
| M     = 000006 | MEMEND= 000040 | MEMST.= 010000 |
| MEMST  000177 | POWERU 000000 | PSW   = 000006 |
| SP    = 000006 | $CHANS= 000020 | $CLEAR= 000002 |
| $DSPSE= 000001 | $FASTL= 000001 | $FASTR= 000002 |
| $FUNCS= 000040 | $MODES= 000100 | $PLOT = 000040 |
| $SLOWL= 000004 | $SLOWR= 000010 | $START= 000004 |
| $STOP = 000010 | $TEST = 000200 | $ZERO = 000020 |
| $1KCNT= 000010 | $1KSAM= 000040 | $1TRIG= 000001 |
| $1UV  = 000020 | $10TRI= 000010 | $10UV = 000200 |
| $100CN= 000001 | $2KSAM= 000100 | $2TRIG= 000002 |
| $2UV  = 000040 | $200CN= 000002 | $5KSAM= 000200 |
| $5TRIG= 000004 | $5UV  = 000100 | $500CN= 000004 |
| $500SA= 000020 | .BLANK= 100033 | .CHAN1= 100022 |
| .CHAN2= 100023 | .CLOCK= 100024 | .OFFPL= 100035 |
| .ONPLO= 100034 | .PORT1= 100026 | .PORT2= 100027 |
| .PORT3= 100030 | .PORT4= 100031 | .STROB= 100025 |
| .SW1  = 100014 | .SW2  = 100015 | .SW3  = 100016 |
| .SW4  = 100017 | .UNBLA= 100032 | .XOUT = 100020 |
| .YOUT = 100021 | .1AMPD= 100010 | .1CNTD= 100000 |
| .1LATD= 100004 | .2AMPD= 100011 | .2CNTD= 100001 |
| .2LATD= 100005 | .3AMPD= 100012 | .3CNTD= 100002 |
| .3LATD= 100006 | .4AMPD= 100013 | .4CNTD= 100003 |
| .4LATD= 100007 | | |
| . ABS. 000460  000 | | |
|         000000  001 | | |

```
        ; I/O DEFINITIONS:
        ;
100000          .1CNTDSP=100000 ;AVERAGE COUNT DISPLAY DIGITS 1-4
100001          .2CNTDSP=100001
100002          .3CNTDSP=100002
100003          .4CNTDSP=100003
        ;
100004          .1LATDSP=100004 ;RELATIVE LATENCY DISPLAY DIGITS 1-4
100005          .2LATDSP=100005
100006          .3LATDSP=100006
100007          .4LATDSP=100007

100010          .1AMPDSP=100010 ;RELATIVE AMPLITUDE DISPLAY DIGITS 1-4
100011          .2AMPDSP=100011
100012          .3AMPDSP=100012
100013          .4AMPDSP=100013
        ;
100014          .SW1=100014     ;SWITCH BUFFER 1
000001          $DSPSEL=1       ; 1=INPUT, 0=AVERAGE
000002          $CLEAR=2
000004          $START=4
000010          $STOP=10
000020          $ZERO=20
000040          $PLOT=40
000100          $MODESEL=100    ; 1=SPECIAL, 0=AVERAGER
000200          $TEST=200       ; 1=NORMAL, 0=DIAGNOSTIC
        ;
100015          .SW2=100015     ;SWITCH BUFFER 2
000001          $FASTLF=1       ; CURSOR FAST LEFT
000002          $FASTRT=2       ; CURSOR FAST RIGHT
```

```
000004          $SLOWLF=4         ; CURSOR SLOW LEFT
000010          $SLOWRT=10        ; CURSOR SLOW RIGHT
000020          $CHANSEL=20       ; 1=CHANNEL 2, 0=CHANNEL 1
000040          $FUNCSEL=40       ; 1=REFERENCE CURSOR, 0=LATENCY CURSOR
100016          .SW3=100016       ; SWITCH BUFFER 3
000001          $100CNT=1         ; AVG STOP COUNT=100
000002          $200CNT=2         ; AVG STOP COUNT=200
000004          $500CNT=4         ; AVG STOP COUNT=500
000010          $1KCNT=10         ; AVG STOP COUNT=1K (2K IF NO BIT ON)
000020          $500SAMP=20       ; SAMPLE RATE=500HZ
000040          $1KSAMP=40        ; SAMPLE RATE=1KHZ
000100          $2KSAMP=100       ; SAMPLE RATE=2KHZ
000200          $5KSAMP=200       ; SAMPLE RATE=5KHZ (10KHZ IF NO BIT ON)

100017          .SW4=100017       ; SWITCH BUFFER 4
000001          $1TRIG=1          ; TRIGGER RATE=1HZ
000002          $2TRIG=2          ; TRIGGER RATE=2HZ
000004          $5TRIG=4          ; TRIGGER RATE=5HZ
000010          $10TRIG=10        ; TRIGGER RATE=10HZ (EXT IF NO BIT ON)
000020          $1UV=20           ; VERTICAL SCALE=1UV FULL SCALE
000040          $2UV=40           ; VERTICAL SCALE=2UV
000100          $5UV=100          ; VERTICAL SCALE=5UV
000200          $10UV=200         ; VERTICAL SCALE=10UV (20UV IF NO BIT ON

100020          .XOUT=100020      ; OUTPUT TO X D/A
100021          .YOUT=100021      ; OUTPUT TO Y D/A
100022          .CHAN1=100022     ; INPUT FROM CHANNEL 1 A/D
100023          .CHAN2=100023     ; INPUT FROM CHANNEL 2 A/D
100024          .CLOCK=100024     ; CLOCK CONTROL
100025          .STROBE=100025    ; PORT 1 OUTPUT STROBE
100026          .PORT1=100026     ; PORT 1 OUTPUT LATCH
100027          .PORT2=100027     ; PORT 2 INPUT BUFFER
100030          .PORT3=100030     ; PORT 3 INPUT BUFFER
100031          .PORT4=100031     ; PORT 4 INPUT BUFFER
100032          .UNBLANK=100032   ; UNBLANK SCOPE
100033          .BLANK=100033     ; BLANK SCOPE
100034          .ONPLOT=100034    ; ENABLE PLOTTER OUTPUTS
100035          .OFFPLOT=100035   ; DISABLE PLOTTER OUTPUTS
```

As another modification, the sequence of steps by which logical controller 40 automatically performs the vision test is not limited to that described in conjunction with FIG. 7. For example, logical controller 40 may perform specialized sequences depending upon whether the patient already has a lens prescription, or whether the patient has some particular eye disease such as glaucoma. Such special testing sequences could be stored in read only memory (ROM) chips includes within controller 40. Therefore, since many changes and modifications can be made to the above details without departing from the nature and spirit of the invention, it is to be understood that the invention is to be limited only as set forth in the appended claims:

Having described my invention, I now claim:

1. An apparatus for automatically testing a patient's vision, said apparatus being comprised of:
   optical means including a target, at least one lens, and an eyepiece serially aligned along one optical path, with said lens or said target having movable positions along said optical path;
   drive means for moving said target or said lens to selectable positions along said optical path in response to first digital control signals;
   light means for enabling light stimulus to be directed along said optical path through said target, said lens, and said eyepiece at each of said selectable positions in response to second digital control signals; and
   digital control means including output means coupled to said drive means and to said light means for generating said first and second digital control signals in a predetermined sequence, input means for receiving electrical signals evoked in the brain of said patient by said light stimulus, and means for measuring the time delay between said light stimulus and said evoked response at each of said selectable positions.

2. Apparatus according to claim 1 wherein said drive means includes decoder means for decoding said first digital control signals, pulse generator means for generating an output pulse of predetermined width in response to the decoding of said control signals, and a motor for moving said target or lens by a distance proportioned to said pulse width.

3. Apparatus according to claim 2, wherein said drive means further includes encoder means coupled to a shaft on said motor for generating signals to said control means indicating the position of said shaft and said target or lens connected thereto.

4. Apparatus according to claim 1 wherein said light means includes decoder means for decoding said second digital control signals, and light driver means coupled to a light source means for generating a light stimulus through said optical means in response to the decoding of said second digital control signals.

5. Apparatus according to claim 4 wherein said light means further includes feedback means coupled to said light driver means for generating signals to said control means indicating a reference point in time from which to measure said time delay of said evoked response.

6. Apparatus according to claim 1 wherein said means for generating said control signals in a predetermined sequence includes means for generating said first control signals to move said target in increments along said optical paths, and means for generating said second control signals to obtain said evoked response at each position of said target.

7. Apparatus according to claim 1 wherein said means for generating said control signals in a predetermined sequence includes means for generating said first control signals to move one of said lens in increments along said optical path, and means for generating said second control signals to obtain said evoked response at each position of said lens.

8. Apparatus according to claim 1 wherein said means for generating said control signals in a predetermined sequence includes means for generating said first control signals to rotate selected ones of said lens in increments about said path, and means for generating said second control signals to obtain said evoked response at each position of said lens.

9. Apparatus according to claim 1 wherein said control means is a microprocessor.

* * * * *